US006254269B1

(12) United States Patent
Ernstson et al.

(10) Patent No.: US 6,254,269 B1
(45) Date of Patent: Jul. 3, 2001

(54) DOSING DEVICE FOR MIXING IN A CONTINUOUS PROCESS A FLOWING PRIMARY LIQUID WITH ONE OR MORE ADDED SECONDARY LIQUIDS

(75) Inventors: Georg Ernstson, Staffanstorp; Johan Sjöholm; Lars Dahlberg, both of Lund, all of (SE)

(73) Assignee: Arom Pak Aktiebolag, Lund (SE)

( * ) Notice: Subject to any disclaimer, the term of this patent is extended or adjusted under 35 U.S.C. 154(b) by 0 days.

(21) Appl. No.: 09/204,055

(22) Filed: Dec. 3, 1998

Related U.S. Application Data

(63) Continuation of application No. PCT/SE97/00965, filed on Jun. 3, 1997.

(30) Foreign Application Priority Data

Jun. 3, 1996 (SE) .................................................. 9602179

(51) Int. Cl.[7] ............................ B01F 15/02; B01F 15/04; A61M 37/00

(52) U.S. Cl. .................................... 366/152.2; 366/160.2; 366/167.1; 366/181.5; 366/174.1; 366/182.2; 604/86; 604/88

(58) Field of Search ............................. 366/152.1, 152.2, 366/160.1, 160.2, 160.3, 167.1, 181.6, 176.1, 182.2, 181.5, 174.1, 336, 340, 175.2; 600/578, 579; 604/486, 88

(56) References Cited

U.S. PATENT DOCUMENTS

| | | | |
|---|---|---|---|
| 4,410,321 | * 10/1983 | Pearson et al. . | |
| 4,585,435 | * 4/1986 | Vaillancourt . | |
| 5,145,250 | * 9/1992 | Planck et al. . | |
| 5,232,437 | * 8/1993 | Lysaght et al. . | |
| 5,378,227 | * 1/1995 | O'Riordan et al. . | |
| 5,407,269 | * 4/1995 | Sherry et al. ...................... | 366/174.1 |
| 5,670,057 | * 9/1997 | Chen et al. . | |
| 5,865,537 | * 2/1999 | Streiff et al. . | |

FOREIGN PATENT DOCUMENTS 9 116138 10/1991 (WO) .

* cited by examiner

*Primary Examiner*—Tony G. Soohoo
(74) *Attorney, Agent, or Firm*—Birch, Stewart, Kolasch & Birch, LLP

(57) ABSTRACT

The present invention relates to a dosing device, or mixing device for mixing, in a continuous process, a flowing primary liquid with one or more added secondary liquids of a smaller quantity for obtaining a flowing liquid mixture at a permanent uniform mixing ratio of the mixed liquids.

27 Claims, 3 Drawing Sheets

DOSING DEVICE FOR MIXING IN A CONTINUOUS PROCESS A FLOWING PRIMARY LIQUID WITH ONE OR MORE ADDED SECONDARY LIQUIDS

This application is a continuation of PCT application no. PCT/SE97/00965 filed on Jun. 3, 1997, which designated the United States and on which priority is claimed under 35 U.S.C. §120, the entire contents of which are hereby incorporated by reference.

BACKGROUND OF THE INVENTION

The present invention relates to a dosing device or mixing device for mixing, in a continuous process, a flowing primary liquid with one or more added secondary liquids for obtaining a flowing liquid mixture at a permanent, uniform mixing ratio of the mixed liquids. Especially, the processing industry and medicinal technology require access to dosing devices, by means of which two or more components in liquid state are continuously mixed with each other under conditions which yield uniform mixing ratios, i.e. uniform amounts of the components included, in a continuous mixing process. The device and the method according to the present invention are especially applicable in the cases where one or some components, so-called secondary components, are to be admixed to a flowing primary component and where the amount of secondary components in terms of volume is comparatively small or very small compared with the amount of the primary component in the finished mixture. In some cases, it is thus desirable to add enzymes, colorants, flavoring agents, vitamins etc. In a flowing quantity of liquid, the content of the added substances, the so-called secondary components, can be as low as 0.05–1% of the flowing primary component. It is possible by using the inventive method to obtain, with a uniform and continuous mixing ratio, a flow of liquid which can proceed to be packed with an equal content of additives in all packings. An example of such a process is, for instance, the preparation of lactose-free sterile milk, where the untreated sterilized and lactose-containing milk is continuously mixed with a quantity of sterile-filtered lactase before packing, the proportions of lactose-containing milk/lactase being in the order of 5–10,000, about the same mixing ratio being required in all packings that are continuously prepared. In some other cases, higher contents of secondary liquid are required as addition, for instance when colorants or flavoring foodstuffs.

Dosing equipment for mixing flows of liquid having different flow ratios is known, but such equipment has essentially been directed to obtaining a constant mixing ratio by letting the combined flows of liquid being joined and conducted in a loop, i.e. a certain part of the flow of liquid is deflected from the main conduit and recirculated to a point in the flow conduit which is positioned downstream. The mixed liquid or parts thereof will in this manner circulate several times through the loop to obtain a good mixing when the loop has finally been passed. The present invention, which operates without a mixing loop, is considerably simpler in its technical design and permits great flexibility as regards the amount and type of additives and is, above all, easier to adjust between the use of different mixing components. The dosing device according to the present invention preferably is adapted to be used in the foodstuff industry but may also be used in medicinal industry for continuous mixing of components in liquid state.

BRIEF DESCRIPTION OF THE DRAWINGS

An embodiment of the invention will be described below with reference to the accompanying schematic drawing, in which.

DESCRIPTION OF THE PREFERRED EMBODIMENTS

As mentioned above, the described device comprises a means for mixing, with great accuracy to volume, a first liquid, here called a primary liquid, with the second liquid, here called a secondary liquid, the mixing ratio being such that there is a very great difference between the individual volumes of the mixed liquids. As pointed out above, in many medicinal processes but also in connection with other processes, for instance, coloring of a liquid or adding of e.g. enzymes or flavoring agents to a liquid, there is a need of adding a smaller amount of secondary liquid to an essentially larger amount of primary liquid. In a continuous mixing process, it is most important that the mixing ratio, in spite of the differences in volume between the mixed liquids, be constant and controllable all the time during the process, such that, for instance, the flavor or the enzyme content of the resulting mixed liquid will not vary.

Figure 1:
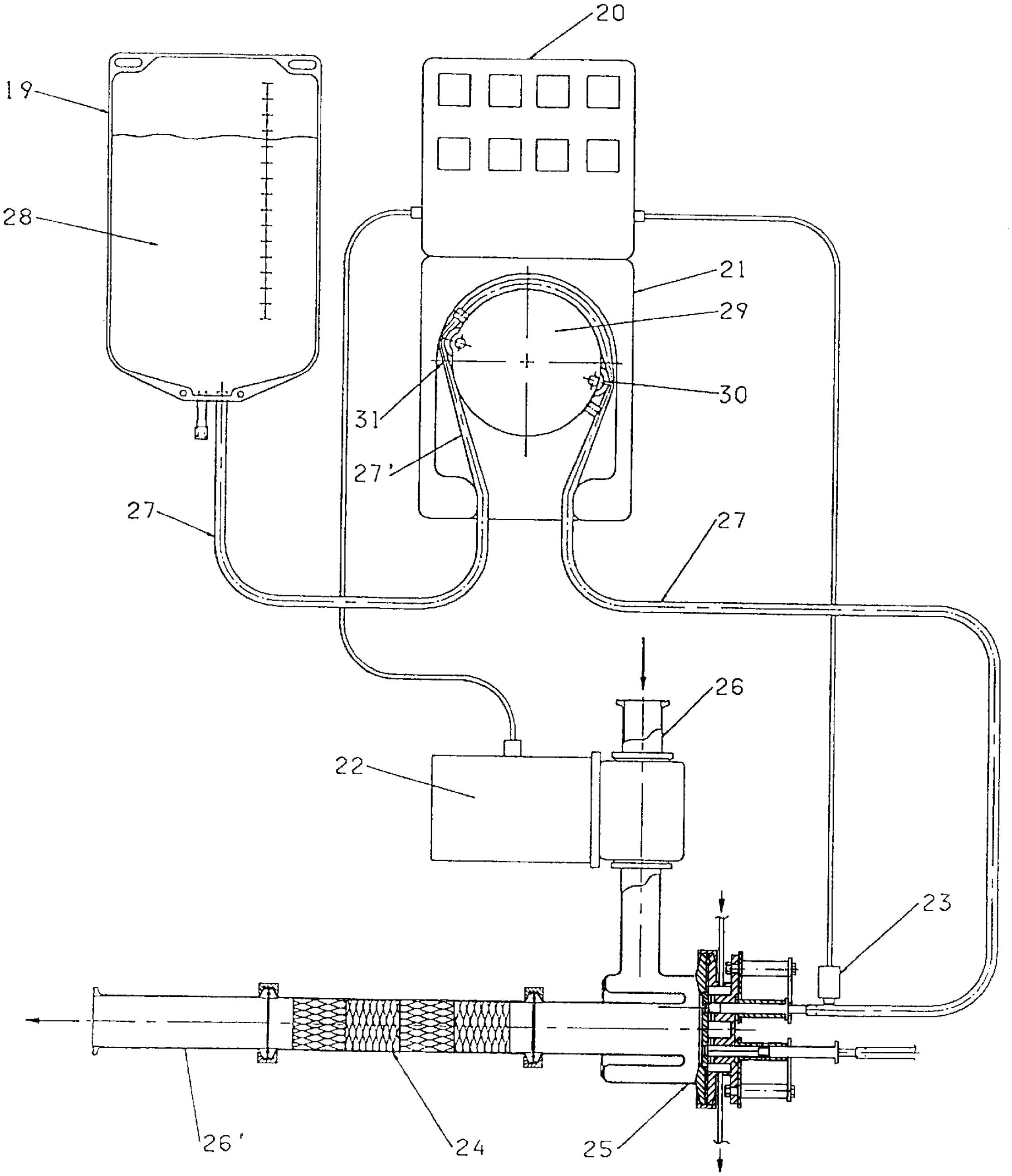
FIG. 1 illustrates the dosing device.

The apparatus shown in FIG. 1 consists of a flow pipe 26 for a primary liquid, the amount of passing primary liquid being controllable by means of a flow meter 22, which registers the amount of passing primary liquid and which by means of the regulator 20 controls the speed of the peristaltic pump 21. In the case shown, the secondary liquid is taken from a plastic bag 19 containing, in this case, sterilized secondary liquid 28. The secondary liquid 28 is passed via the conduit 27 to a peristaltic pump 21 controlled by the regulator 20 and being of known type. This peristaltic pump 21 comprises a rotatable cylindrical body 29, which at its circumference supports rollers 30. In the case shown, the rollers 30 are positioned diametrically opposite each other in the cylindrical body 29 rollers project outside the periphery of the rotatable body 29. At least part 27' of the conduit 27 is made of a flexible material, e.g. rubber or plastic, and this part 27' of the conduit 27 is arranged in a duct 31 of the pump 21.

During rotation of the cylindrical body 29, the flexible conduit 27' is compressed by the rollers 30, the liquid contained in the conduit 27' between the rollers 30 being pressed forwards by the rollers 30 in the direction of rotation of the cylindrical body 29 and thus being pumped forwards. Since the dimension of the tube 27' is known and the speed of rotation of the cylindrical body 29 is controllable, the amount of pumped liquid in the conduit 27 can be very accurately controlled and the flow can be kept very constant. In order to stop the pump 21 and the mixing process if the flow in the conduit 27 is interrupted, a flow control device 23 is arranged at or in the vicinity of the terminal point of the conduit 27. The secondary liquid 28 supplied as described above is added to the primary liquid by means of a specially arranged inlet chamber 25 which is shown in detail in FIG. 2. The inlet chamber 25, which is connected to the conduit 26 for the primary liquid, is provided with a conduit flange 32, which is located in the position where the conduit 26 in the case shown makes a bend and, in the bend of the conduit, has a liquid-flow-conducting labyrinth 41 for guiding the flow of primary liquid towards the inlet chamber 25. The inlet chamber 25 is provided with a connecting flange 33, which matches the connecting flange 32 and which is provided with seals 34 closely connected to each other. The inlet chamber 25 also has spaces 35, which can be kept sterile by means of a sterilizing agent, e.g. vapor or a sterilizing liquid, supplied through the conduit 10. The passing vapor or liquid sterilizes the spaces 35 and all the objects that are present or may be present in the spaces 35. Moreover, the inlet chamber 25 has one or more spaces 14, which are adapted to receive injection needles or syringe-like cannulae comprising a hypodermic needle 12 and a connection 36 to the conduit 27.

Figure 2:
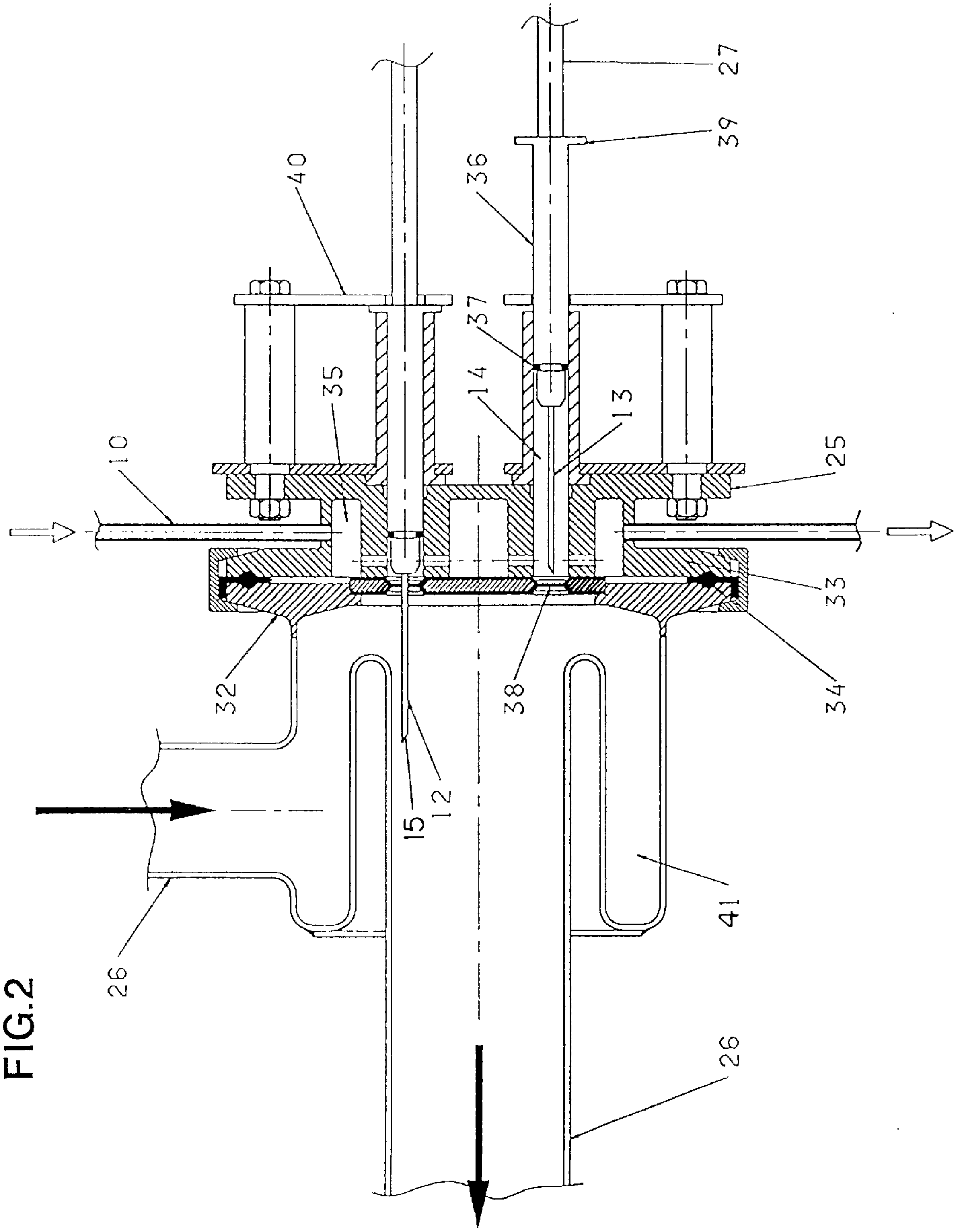
FIG. 2 illustrates a special device with a plurality of needle-like nozzles for supplying a secondary liquid and FIG. 3 shows a flexible plastic bag for storing sterilized secondary liquid.

As shown in FIG. 2, the inlet chamber 25 may be provided with several spaces 14 for hypodermic needle arrangements which, adjacent to said connection 36, are sealed against the inlet chamber 25 by means of a sealing ring 37 of O-ring type.

Figure 3:
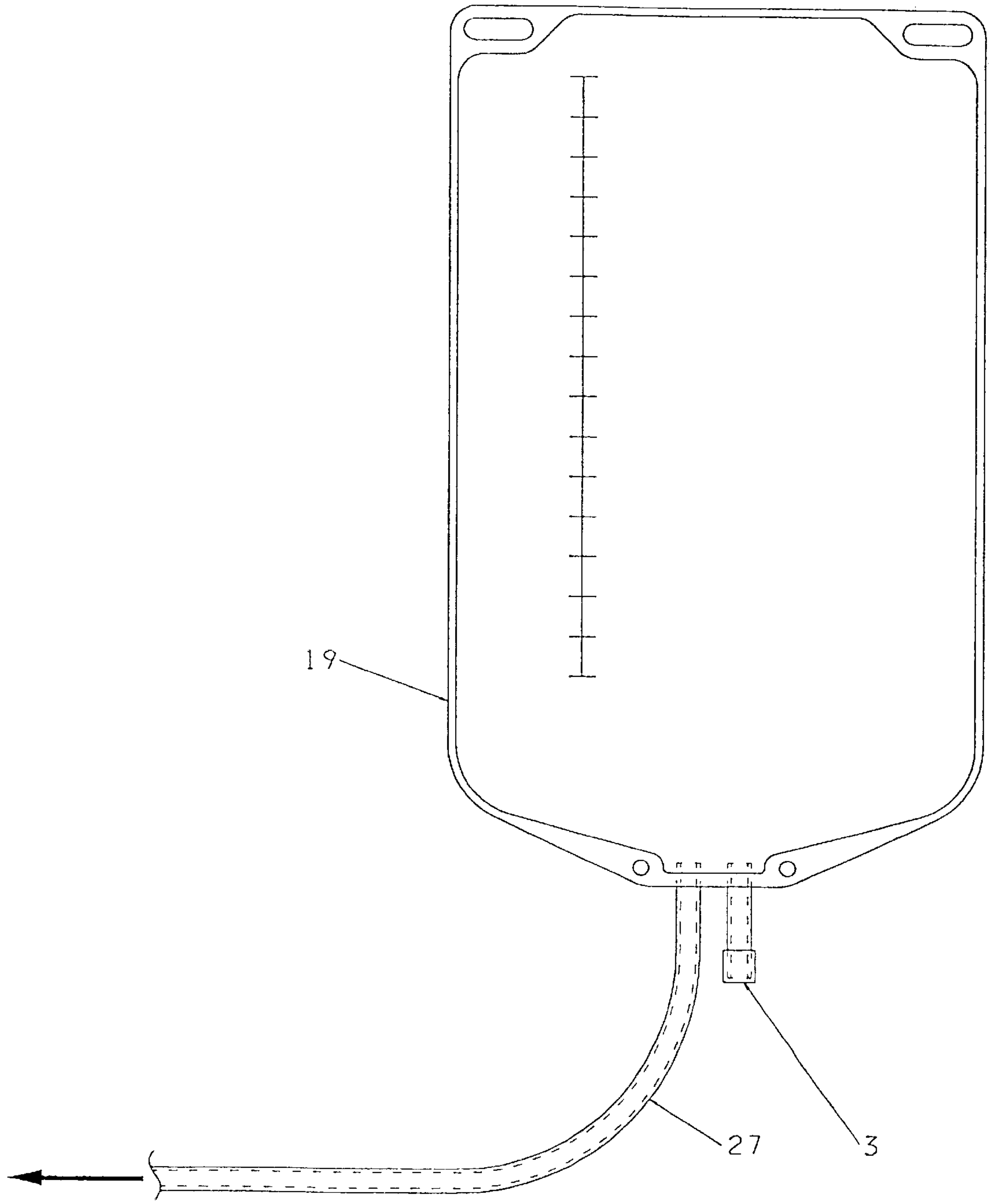

The cannula including an obliquely cut-off portion 15, is thus displaceably movable in the spaces 14 by displacing the connection 36 with the sealing ring 37. That part of the inlet chamber 25 which connects to the primary liquid conduit 26 has a sealing wall 38 made of rubber or a rubber-like material, which can easily be penetrated by the cannula 12 and which, after retraction of the cannula 12 into the space 14, in a self-sealing manner attaches itself around the hole made by the cannula 12 in the sealing wall 38. Thus, the cannula 12 can, when positioned in the space 14, be sterilized and be made to retain its sterility to be passed through the sealing wall 38 into the conduit 26 for supplying, in an accurately predetermined dose, secondary liquid 28 to the flowing primary liquid. The cannula 12 can also be retracted into the space 14 without interruption of the sterility. As shown, the connection 36 to the cannula 12, 13 is provided with a flange 39. After insertion of the cannula 12, 13 into the conduit 26, the cannula 12, 13 can be locked in the inserted position by a stop flange 40 being pushed over the flange 39, the position of the cannula 12 and the associated connection 36 being fixed. To achieve a good mixing of primary liquid and secondary liquid or secondary liquids, the conduit 26' for the mixed liquids is provided with a mixing chamber 24 having surfaces deflecting the flow of liquid to achieve, under turbulent flow, a homogeneous mixing of the joined liquids. FIG. 3 shows an example of the above-described bag 19 for the secondary liquid, and as is obvious, the bag is provided with two connections 27, 3, the connection 3 constituting the filling conduit and the tube 27, as described above, constituting the discharge conduit for secondary liquid. Of course, the tank for secondary liquid 19 need not necessarily be a plastic bag but may be a more dimensionally stable vessel made of plastic or metal, and it is not necessary to the invention that the supplied secondary liquid or, for that matter, the primary liquid be a sterile liquid.

It should be added that in the cases where several secondary liquids are to be supplied, not only the inlet chamber must be provided with several chambers and cannulae for the secondary liquid 28, but also that each secondary liquid 28 necessitates its own storage tank 19, its own pump 21 and its own regulator 20, unless the secondary liquids are not of such a nature that even in the storage tank they can be mixed to a common "secondary liquid mixture". An inlet chamber with a number of cannula positions may be practical to use with a view to making it possible to stop the process without shifting from a secondary liquid tank 19 to another when the first tank is empty. Such a "flying shift" of the secondary liquid tank 19 is possible to perform if the inlet chamber 25 is provided with several cannula spaces in the manner as described above.

It has been found that the device according to the present invention results in a permanent, very exact mixing ratio also during long continuous operation even if the volume ratio when mixing the liquids is extremely nonuniform.

As mentioned, it is also possible to mix, under uninterruptedly aseptic conditions, sterile liquids, and it is also easy during the mixing operation, if desired, to adjust the mixing ratio with very great accuracy.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A dosing device for mixing, in a continuous process, a flowing primary liquid with at least one added secondary liquid of an essentially smaller quantity 0.05–1% for obtaining a flowing liquid mixture at a permanent uniform mixing ratio of the mixed liquids, comprising:

a flow pipe through which the primary liquid is flowable, said flow pipe including a perforated wall part having a penetratable, flexible wall part arranged therein, said penetrable, flexible wall part being located at a portion of said flow pipe through which said primary liquid is flowable;

a mixing chamber arranged in said flow pipe or connected in series therewith;

at least one narrow nozzle insertable into said flow pipe and including at least one needle-shaped tube, said at least one narrow nozzle being insertable into the flow pipe through said penetratable, flexible wall part;

at least one storage tank for holding said at least one secondary liquid; and at least one pump for continuously supplying said at least one secondary liquid from said at least one storage tank to said at least one narrow nozzle.

2. The dosing device according to claim 1, wherein said at least one narrow nozzle is located in parallel with a flow path of the primary liquid and centrally arranged therein when said at least one narrow nozzle is in an inserted position.

3. The dosing device according to claim 1, wherein each of said at least one narrow nozzle includes injection-needle-shaped devices each having an obliquely cut-off pointed portion and having inlet openings provided with connecting means for connecting the injection-needle-shaped devices to tubes or conduits for supplying said at least one secondary liquid.

4. The dosing device according to claim 1, wherein each of said at least one storage tank is a sterilized bag or a non-yielding container made of a flexible plastic material or metal, and the contents of said at least one storage tank includes a sterile liquid.

5. The dosing device according to claim 4, wherein each of said at least one storage tank has two connection ducts in the form of tubes or conduit connected thereto, said connection ducts communicating with an interior of said at least one storage tank, respectively, one of said communication ducts is a supply duct and the other of said communication ducts is a liquid-discharging duct, and each of the connection ducts is adapted to permit separate closing and opening.

6. The dosing device according to claim 1, wherein said at least one pump is a peristaltic pump having an infinitely variably adjustable pump capacity by means of a regulator controlling a speed of rotation of the pump.

7. The dosing device according to claim 1, further comprising:

a flow meter for measuring a flow of the primary liquid in said flow pipe; and a regulator controlled by said flow meter for regulating a speed of rotation, and thus, the flow from said at least one pump such that said at least one secondary liquid is admixed with the primary liquid in a controllable manner and in a controllable quantity.

8. The dosing device according to claim 1, further comprising:

a connection means for supplying said at least one secondary liquid, said connection means including a holder connectable to said flow pipe and for receiving said at least one needle-shaped tube, said holder including at least two guide sleeves adapted to support and longitudinally guide a position of said at least one needle-shaped tube, each of said at least one needle-shaped tube being slidably attached in said sleeves, an interior of said sleeves in a longitudinal extension thereof being open at said penetratable, flexible wall part, said penetratable, flexible wall part separating said sleeves from an interior of said flow pipe, said at least one needle-shaped tube being individually operable in said sleeves, respectively, such that, independently of each other, said at least one needle-shaped tube can be moved in a longitudinal direction of said at least one narrow nozzle and be caused to penetrate said penetratable, flexible wall part to locate a point of said at least one needle-shaped tube in said flow pipe to supply said at least one secondary liquid to said primary liquid.

9. A dosing device for mixing, in a continuous process, a flowing primary liquid with at least one added secondary liquid of an essentially smaller quantity 0.05–1% for obtaining a flowing liquid mixture at a permanent uniform mixing ratio of the mixed liquids, comprising:

a flow pipe through which the primary liquid is flowable, said flow pipe including a perforated wall part having a penetratable, flexible wall part arranged therein, said penetrable, flexible wall part being located at a portion of said flow pipe through which said primary liquid is flowable;

a mixing chamber arranged in said flow pipe or connected in series therewith, said mixing chamber having a plurality of deflection parts located in said flow pipe and for deflecting a direction of flow for partial amounts of said primary liquid and said at least one secondary liquid to produce a turbulent flow and obtain a homogeneous mixing of the liquids supplied;

at least one narrow nozzle insertable into said flow pipe and including at least one needle-shaped tube, said at least one narrow nozzle being insertable into the flow pipe through said penetratable, flexible wall part;

at least one storage tank for holding said at least one secondary liquid; and at least one pump for continuously supplying said at least one secondary liquid from said at least one storage tank to said at least one narrow nozzle.

10. The dosing device according to claim 9, wherein said at least one narrow nozzle is located in parallel with a flow path of the primary liquid and centrally arranged therein when said at least one narrow nozzle is in an inserted position.

11. The dosing device according to claim 9, wherein each of said at least one narrow nozzle includes injection-needle-shaped devices each having an obliquely cut-off pointed portion and having inlet openings provided with connecting means for connecting the injection-needle-shaped devices to tubes or conduits for supplying said at least one secondary liquid.

12. The dosing device according to claim 9, wherein each of said at least one storage tank is a sterilized bag or a non-yielding container made of a flexible plastic material or metal, and the contents of said at least one storage tank includes a sterile liquid.

13. The dosing device according to claim 12, wherein each of said at least one storage tank has two connection ducts in the form of a tube or conduit connected thereto, said connection ducts communicating with an interior of said at least one storage tank, respectively, one of said communication ducts is a supply duct and the other of said communication ducts is a liquid-discharging duct, and each of the connection ducts is adapted to permit separate closing and opening.

14. The dosing device according to claim 9, wherein said at least one pump is a peristaltic pump having an infinitely variably adjustable pump capacity.

15. The dosing device according to claim 9, further comprising:

a flow meter for measuring a flow of the primary liquid in said flow pipe; and a regulator controlled by said flow meter for regulating a speed of rotation, and thus, the flow from said at least one pump such that said at least one secondary liquid is admixed with the primary liquid in a controllable manner and in a controllable quantity.

16. The dosing device according to claim 9, wherein a space is formed adjacent said penetratable, flexible wall part through which a sterilizing liquid is flowable, said sterilizing liquid, at least during insertion of said at least one needle-shaped tube through said penetratable, flexible wall part, surrounding or flowing around a part of said at least one needle-shaped tube insertable through said penetratable, flexible wall part.

17. The dosing device according to claim 16, wherein said space is filled with sterilizing liquid and is defined by an outlet wall including said penetratable, flexible wall part, said at least one needle-shaped tube being surrounded by or flushed with said sterilizing liquid, before penetration of the outlet wall of said space, and said at least one needle-shaped tube is caused to penetrate said outlet wall into said flow pipe through further movement in the longitudinal direction of said at least one narrow nozzle.

18. The dosing device according to claim 9, further comprising:

a connection means for supplying said at least one secondary liquid, said connection means including a holder connectable to said flow pipe and for receiving said at least one needle-shaped tube, said holder including at least two guide sleeves adapted to support and longitudinally guide a position of said at least one needle-shaped tube, each of said at least one needle-shaped tube being slidably attached in said sleeves, an interior of said sleeves in a longitudinal extension thereof being open at said penetratable, flexible wall part, said penetratable, flexible wall part separating said sleeves from an interior of said flow pipe, said at least one needle-shaped tube being individually operable in said sleeves, respectively, such that, independently of each other, said at least one needle-shaped tube can be moved in a longitudinal direction of said at least one narrow nozzle and be caused to penetrate said penetratable, flexible wall part to locate a point of said at least one needle-shaped tube in said flow pipe to supply said at least one secondary liquid to said primary liquid.

19. A dosing device for mixing, in a continuous process, a flowing primary liquid with at least one added secondary liquid of an essentially smaller quantity 0.05–1% for obtaining a flowing liquid mixture at a permanent uniform mixing ratio of the mixed liquids, comprising:

a flow pipe through which the primary liquid is flowable, said flow pipe including a perforated wall part having a penetratable, flexible wall part arranged therein, said penetrable, flexible wall part being located at a portion of said flow pipe through which said primary liquid is flowable;

a space formed adjacent said penetratable, flexible wall part through which a sterilizing liquid is flowable, said space being in communication with a conduit for sterilizing liquid, said sterilizing liquid, at least during insertion of said at least one needle-shaped tube through said penetratable, flexible wall part, surrounding or flowing around a part of said at least one needle-shaped tube insertable through said penetratable, flexible wall part;

a mixing chamber arranged in said flow pipe or connected in series therewith;

at least one narrow nozzle insertable into said flow pipe and including at least one needle-shaped tube, said at least one narrow nozzle being insertable into the flow pipe through said penetratable, flexible wall part;

at least one storage tank for holding said at least one secondary liquid; and at least one pump for continuously supplying said at least one secondary liquid from said at least one storage tank to said at least one narrow nozzle.

20. The dosing device according to claim 19, wherein said at least one narrow nozzle is located in parallel with a flow path of the primary liquid and centrally arranged therein when said at least one narrow nozzle is in an inserted position.

21. The dosing device according to claim 19, wherein each of said at least one narrow nozzle includes injection-needle-shaped devices each having an obliquely cut-off pointed portion and having inlet openings provided with connecting means for connecting the injection-needle-shaped devices to tubes or conduits for supplying said at least one secondary liquid.

22. The dosing device according to claim 19, wherein each of said at least one storage tank is a sterilized bag or a non-yielding container made of a flexible plastic material or metal, and the contents of said at least one storage tank includes a sterile liquid.

23. The dosing device according to claim 22, wherein each of said at least one storage tank has two connection ducts in the form of a tube or conduit connected thereto, said connection ducts communicating with an interior of said at least one storage tank, respectively, one of said communication ducts is a supply duct and the other of said communication ducts is a liquid-discharging duct, and each of the connection ducts is adapted to permit separate closing and opening.

24. The dosing device according to claim 19, wherein said at least one pump is a peristaltic pump having an infinitely variably adjustable pump capacity.

25. The dosing device according to claim 19, further comprising:

a flow meter for measuring a flow of the primary liquid in said flow pipe; and a regulator controlled by said flow meter for regulating a speed of rotation, and thus, the flow from said at least one pump such that said at least one secondary liquid is admixed with the primary liquid in a controllable manner and in a controllable quantity.

26. The dosing device according to claim 25, wherein said space is filled with sterilizing liquid and is defined by an outlet wall including said penetratable, flexible wall part, said at least one needle-shaped tube being surrounded by or flushed with said sterilizing liquid, before penetration of the outlet wall of said space, and said at least one needle-shaped tube is caused to penetrate said outlet wall into said flow pipe through further movement in the longitudinal direction of said at least one narrow nozzle.

27. The dosing device according to claim 19, further comprising:

a connection means for supplying said at least one secondary liquid, said connection means including a holder connectable to said flow pipe and for receiving said at least one needle-shaped tube, said holder including at least two guide sleeves for defining said space and adapted to support and longitudinally guide a position of said at least one needle-shaped tube, each of said at least one needle-shaped tube being slidably attached in said sleeves, an interior of said sleeves in a longitudinal extension thereof being open at said penetratable, flexible wall part, said penetratable, flexible wall part separating said sleeves from an interior of said flow pipe, said at least one needle-shaped tube being individually operable in said sleeves, respectively, such that, independently of each other, said at least one needle-shaped tube can be moved in a longitudinal direction of said at least one narrow nozzle and be caused to penetrate said penetratable, flexible wall part to locate a point of said at least one needle-shaped tube in said flow pipe to supply said at least one secondary liquid to said primary liquid.

* * * * *